United States Patent [19]
McCormick

[11] 3,939,699
[45] Feb. 24, 1976

[54] TENSIOMETER WITH REMOTE SENSING UNIT

[76] Inventor: John P. McCormick, 521 Hilmar St., Santa Clara, Calif. 95050

[22] Filed: Sept. 27, 1974

[21] Appl. No.: 509,900

[52] U.S. Cl. .............................. 73/73; 73/398 AR
[51] Int. Cl.² .......................................... G01N 7/14
[58] Field of Search ......... 73/73, 74, 323, 325, 401, 73/398 AR

[56] References Cited
UNITED STATES PATENTS

| | | | |
|---|---|---|---|
| 963,150 | 7/1910 | Howell | 73/325 |
| 2,878,671 | 3/1959 | Prosser et al. | 73/73 |
| 3,043,133 | 7/1962 | Richards | 73/73 |
| 3,091,115 | 5/1963 | Roberts | 73/73 |
| 3,349,623 | 10/1967 | Pastan | 73/398 AR |

FOREIGN PATENTS OR APPLICATIONS

| | | | |
|---|---|---|---|
| 766,023 | 8/1967 | Canada | 73/73 |

Primary Examiner—Richard C. Queisser
Assistant Examiner—Marcus S. Rasco
Attorney, Agent, or Firm—John N. Randolph

[57] ABSTRACT

A tensiometer having a vacuum gauge which is connected to a sensing unit including a ceramic cup, which is located remote from said gauge, by a conductor in the form of a capillary tube. A second capillary bleeder tube communicates with and leads from the ceramic cup and has a second end which is located below the level of the other end of the conducting tube, so that when said second end of the bleeder tube is exposed, the escape of air therefrom can be visually determined, during purging of the device, so that after all air has been removed from the tubes, the tensiometer can be sealed. The end of the conducting tube disposed remote from the ceramic cup is connected to a lower end of a sight glass, to the upper end of which is connected the gauge, so that when air has been removed from the device and the sight glass, tubes and cup are filled with water and sealed, a vacuum will be created in the system as the moisture in the earth surrounding the cup diminishes, to register this reduced moisture condition on the gauge.

5 Claims, 3 Drawing Figures

U.S. Patent  Feb. 24, 1976  3,939,699
FIG. 1
FIG. 2
FIG. 3
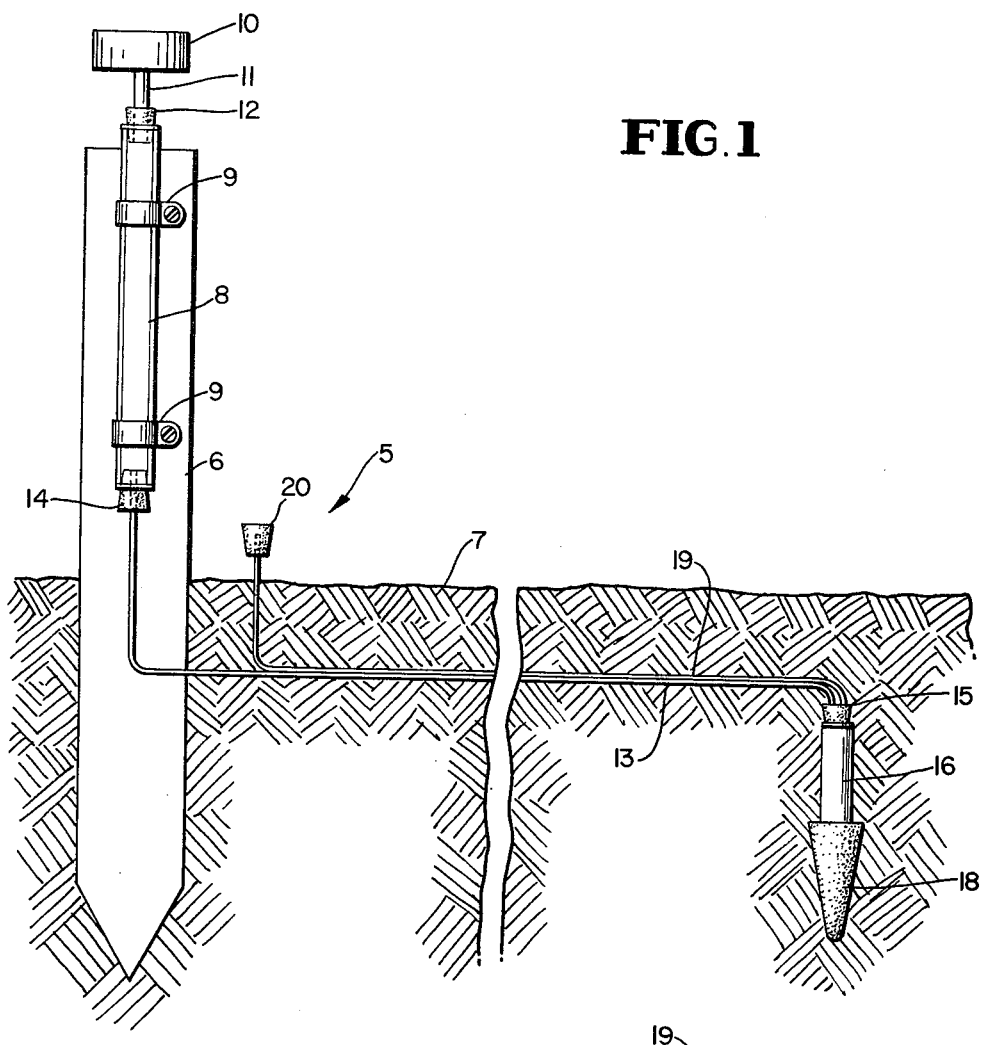
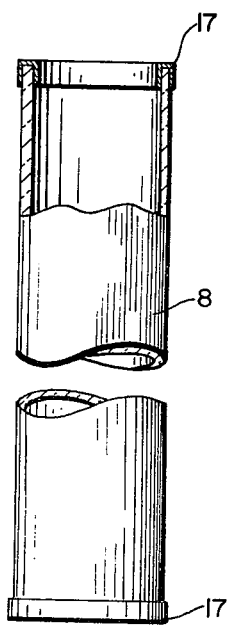
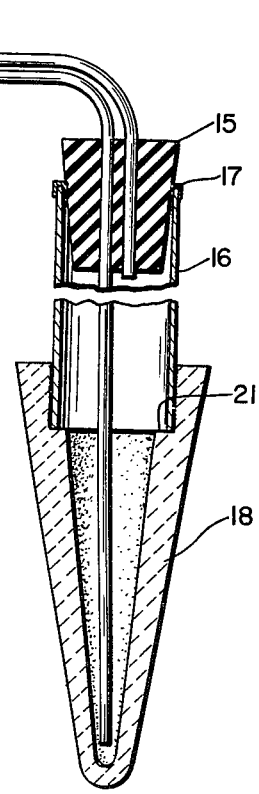

TENSIOMETER WITH REMOTE SENSING UNIT

BACKGROUND OF THE INVENTION

Prior attempts to locate a ceramic cup remote from the vacuum gauge of a tensiometer have been unsuccessful due to the fact that the large diameter tubes utilized have required substantially continuous purging of air therefrom to compensate for leakage of air into the cup. In addition, air locks have occurred due to high spots in the tube from which air could not be removed, thereby resulting in inaccurate readings.

SUMMARY

It is a primary object of the present invention to provide a tensiometer having a remotely located sensing unit connected to the gauge of the tensiometer by capillary tubes whereby, after water has been run through said tubes to exclude all air, the surface tension of the water is sufficient to prevent air from entering the tubes and causing air locks.

A further object of the invention is to provide such a sensing unit wherein the capillary conducting tube may be made flexible so that any jarring of the end thereof, disposed remote from the ceramic cup, will not be conveyed to the cup, thereby eliminating the risk of cup breakage.

A further object of the invention is to provide a tensiometer having a remotely located sensing unit and which utilizes two capillary tubes leading from the sensing unit, and wherein one tube, the conducting tube, connects with the registering unit while the other, bleeder tube, allows the system to be filled with water and purged of air, since the bores of the two capillary tubes are sufficiently small to enable the surface tension of the water to trap and force the air from the system through the tubes.

Various other objects and advantages of the invention will hereinafter become more fully apparent from the following description of the drawing, illustrating a presently preferred embodiment thereof, and wherein:

BRIEF DESCRIPTION OF THE DRAWING

FIG. 1 is a fragmentary side elevational view of the tensiometer with remote sensing unit;

FIG. 2 is an enlarged fragmentary side elevational view, partly in vertical section, of one part of the unit, and FIG. 3 is an enlarged vertical sectional view of the sensing unit of the invention.

DESCRIPTION OF THE PREFERRED EMBODIMENT

Referring more specifically to the drawing, the tensiometer with remote sensing unit in its entirety is designated generally 5 and includes a support 6, such as a stake, one end of which is driven into the earth 7. A transparent tube 8 is fastened by clamps 9 to the stake or support 6 above ground level. The sight glass 8 is preferably formed of clear plastic the ends of which fit into ringshaped metal ferrules 17 which prevent cracking of the plastic when tapered stoppers are forced into the sight glass ends.

A vacuum gauge 10 has a tube extending downwardly from the case thereof. Said tube 11 has a lower end extending through a rubber stopper 12 which is pressed into an upper end of the sight glass 8 to provide a sealed connection between said sight glass end and the gauge 10.

One end of a flexible capillary conducting tube 13 is secured in and extends through a tapered rubber stopper 14 which is pressed into the other, lower end of the sight glass 8 to form a sealed connection. The conducting tube 13 extends from the stopper 14 underground to and through one bore of a rubber tapered stopper 15 which is secured in the upper end of a tube 16. Said upper end of the tube 16 is also provided with a ferrule 17 to prevent the tube 16 from being cracked by the pressure of the stopper 15. The other lower end of the tube 16 seats in a recess 21 of a ceramic cup 18, to which said tube end is bonded.

The cup 18 which is produced by the isostatic process is essential to the successful operation of a tensiometer having a remote sensing unit and which utilizes a capillary conducting tube, since such cups leak much less air than cups produced by the slip cast method. The last mentioned end of the conducting tube 13 extends to nearly the bottom of the cavity of the cup, as seen in FIG. 3.

One end of a flexible capillary bleeder tube 19 extends through and is secured in a second bore of the stopper 15. The other end of the tube 19 projects above the ground level, preferably adjacent the support 6, and terminates below the level of the end of the conducting tube 13 which is secured in the stopper 14. A cap 20, prefereably formed of rubber, has a blind bore or socket into which said last mentioned exposed end of the tube 19 extends and by which said tube end is normally sealed.

The stopper 12 with the gauge 10 is removed from the upper end of the sight glass 8 and the cap 20 is removed from the exposed end of the tube 19. The system is now filled with water through the upper end of the tube 8 until air ceases to escape from the exposed end of the tube 19. If the tube 19 is transparent, this can be readily determined visually. If not, a short transparent tubular extension, not shown, is attached to said end of the tube 19 from which the cap 20 has been removed. Cap 20 is then replaced on the upper end of the tube 19 for sealing said tube end and the sight glass 8 is filled to overflowing, after which the stopper 12 is replaced in the upper end thereof for sealing the system.

A small amount of air is retained in the water in the form of bubbles too small to separate immediately. When a vacuum is applied to the system, due to the earth surrounding the cup 18 losing a part of its moisture, the air bubbles will expand and coalesce into larger bubbles, which can be removed by again purging the system after the vacuum has been released.

Air can also be purged from the system by applying a vacuum thereto. This can be accomplished by purging the system as previously described. The cap 20 is then replaced, after which the sight glass 8 is filled with water and a vacuum pump is attached to the upper end of the sight glass to create a vacuum. This will cause small bubbles formed in the sight glass to coalesce and rise to the top of the sight glass. The vacuum pump can then be removed and the sight glass 8 sealed with the stopper 12, as previously described.

The bores of the tubes 13 and 19 are sufficiently small so that the surface tension of the water will trap and force the air from the system through the tubes. As the bubbles coalesce, they will form air pistons in the tubes which will force the air through the bleeder tube 19 as water is applied to the sight glass 8. The removal of the air from the system increases the reaction time of the tensiometer.

The tube 13 is extended to adjacent the bottom of the cavity of the cup 18 so that the air will be more readily forced from said cavity as water is supplied to the cup through the tube 13.

Various modifications and changes are contemplated and may be resorted to, without departing from the function of scope of the invention.

I claim as my invention:

1. A tensiometer with remote sensing unit comprising a sight glass having an upper end and a lower end, a ceramic cup buried in the earth remote from said sight glass, a flexible capillary conducting tube having one end communicating with the lower end of the sight glass and an opposite end communicating with the cup cavity, means sealing said tube ends in the lower end of the sight glass and in said cup, a closure sealing the upper end of the sight glass, a vacuum gauge supported by said closure and communicating with the interior of the sight glass, said sight glass, tube and cup cavity being filled with water, a second flexible capillary bleeder tube having one end communicating with the cup cavity and sealed in said cup, said blender tube having a second upper end disposed below the level of the end of the conducting tube which is connected to the sight glass, and a removable cap for sealing said upper bleeder tube end.

2. A tensiometer as in claim 1, at least the upper end of said bleeder tube being transparent whereby the escape of air therefrom can be visually determined as the sight glass, tubes and cup cavity are filled with water through the upper end of the sight glass and after removal of said cap.

3. A tensiometer as in claim 1, the end of the conducting tube which communicates with the cup cavity terminating adjacent the bottom of said cup cavity and below the end of the bleeder tube which communicates with the cup cavity.

4. A tensiometer as in claim 3, a tubular extension secured in and projecting from the upper end of the cup cavity, said means for connecting the tubes to the cup and for sealing the cup cavity comprising a tapered stopper having spaced apart bores extending therethrough and in which portions of said tubes are sealed.

5. A tensiometer as in claim 1, a stake-like support adapted to be driven into the earth and to which said sight glass is detachably secured.

* * * * *